United States Patent [19]

Sawada

[11] 4,446,129

[45] May 1, 1984

[54] METHOD FOR TREATMENT OF ARTHROSIS DEFORMANS WITH ELASTASE

[75] Inventor: Tohru Sawada, Ibaragi, Japan

[73] Assignee: Eisai Co., Ltd., Tokyo, Japan

[21] Appl. No.: 529,070

[22] Filed: Sep. 2, 1983

[30] Foreign Application Priority Data

Sep. 17, 1982 [JP] Japan .............................. 57-160837

[51] Int. Cl.³ .............................................. A61K 37/48
[52] U.S. Cl. .................................................... 424/94
[58] Field of Search .......................................... 424/94

[56] References Cited

U.S. PATENT DOCUMENTS 4,397,951 8/1983 Taki et al. .............................. 424/94

Primary Examiner—Sam Rosen
Attorney, Agent, or Firm—Flynn, Thiel, Boutell & Tanis

[57] ABSTRACT

A method is disclosed for treating a subject suffering from arthrosis deformans which comprises administering to said subject a therapeutically effective amount of a composition comprising elastase and a pharmacologically acceptable carrier. Particularly excellent results were obtained using this method for the treatment of gonarthrosis deformans.

10 Claims, No Drawings

METHOD FOR TREATMENT OF ARTHROSIS DEFORMANS WITH ELASTASE

This invention relates to a method and pharmaceutical composition for the treatment of arthrosis deformans containing elastase as an effective ingredient.

Arthrosis deformans, also known as arthritis deformans, is a desease which does not accompany inflammation. The chief lesion thereof or effect is the degeneration of articular cartilage, accompanied by changes such as bone enlargement and bone fibrillation. The mechanism of the development of arthrosis deformans has not yet been elucidated in many respects, but because the development of this disease advances with the age of the patient, the metabolic disturbance of articular cartilage is thought to be an important factor. Namely, the amount of the matrix substances of cartilage, such as proteoglycans, is decreased, and at the same time, granules of mucopolysaccharides or proteins are liberated, which cause thinning of the articular cartilage and separation of collagen. Consequently, the cartilage assumes the form of an asbestos-like fiber, the surface of the articular cartilage becomes frayed in a manner similar to fine villi, and fibrillation of the cartilage occurs. Such changes occur more frequently in load-bearing joints, such as knee joints and hip joints. Accordingly, the aged often suffer from dysbasia due to gonarthralgia. The repair of degenerated articular cartilage is extremely difficult, so that at present, only symptomatic treatment is carried out on patients suffering from arthrosis deformans for the purpose of relieving pain.

The present invention is directed to compositions for treating arthrosis deformans, and particularly compositions for palliating or clearing up arthralgia, which is a clinical characteristic of arthrosis deformans. As a result, it was found that the enzyme elastase achieves these objects.

It is an object of this invention to provide a method for palliating or providing a remission from arthrosis deformans, and particularly for exerting an analgesic effect on arthralgia caused by arthrosis deformans.

Elastase is an enzyme which specifically decomposes elastin, a water-insoluble scleroprotein. Elastase is industrially produced by extraction from swine pancreas. Porcine elastase has the following characteristics. First, porcine elastase has a molecular weight of 25,900, a value determined from the amino acid sequence of the primary structure of the elastase molecule, an isoelectric point of pH 9.5±0.5, and a sedimentation coefficient $S_{20,w}$ of 2.6. As to activity, the porcine elastase molecule contains serine and histidine in its active center and has the property of specifically decomposing the synthetic substrates N-α-benzoyl-L-alanine methyl ester and acetyl-L-trialanine-p-nitroanilide, in addition to elastin. According to results obtained from measurements made using N-α-benzoyl-L-alanine methyl ester as a substrate, the optimal activation pH for elastase is from 8 to 10, particularly about 8.8. The activity of elastase is inhibited by NaCl, KCl, $(NH_4)_2SO_4$, NaCN, $CuSO_4$, and some N-α-benzoylcarboxy derivatives.

As to biochemical properties, elastase has been confirmed to have a β-lipoproteinase activity and a lipoprotein lipase activity, and it exerts a normalizing effect on the disturbance of lipid metabolism in the serum and tissues. Accordingly, in clinical applications, elastase has been used to ameliorate serum lipid anomalies associated with hyperlipemia and arteriosclerosis. Furthermore, elastase maintains and promotes the elasticity and dilatability of arterial walls. In other words, it functions to remove denatured elastin from arterial walls and to promote formation of fresh elastin, and in addition, hinders deposition of fat on the denatured elastin and thereby hinders development of atherosclerosis.

The following literature references describe clinical applications of elastase:

(1) Kazuo Ogawa, Yasuhiro Gosato: Morphological Study on Anti-atherosclerotic Action of Elastase, Nichi Ro Ishi, 10, 277–292 (1973).

(2) Akira Osawa: About Anti-arteriosclerotic Action of Elastase (elastic fiber decomposing enzyme). Nichinai Kaishi, 59, 20–29 (1970).

(3) Shuko Naito, Toshio Tono, Tsutomu Iwabuchi, Yoshie Ishimaru, Akihide Uesugi, Michio Ogasawara, Akimasa Omori, Masao Kase, Hitoshi Kimura, Yasushi Shichiri, Saburo Yokoyama: Study on Effect of Elastase on Improvement of Anomalies of Serum Lipid by Double-Blind Procedure. Igaku no Ayumi, 82, 848–859 (1972).

(4) Toshio Tono: Treatment of Arteriosclerotic Diseases by Elastase. Rinsho to Kenkyu 53, 1798 (1976).

(5) Motoharu Hasegawa, Ken Kawasaki, Chikao Arai et al, Anti-arteriosclerotic Effect of Elastase, Dohmyaku Kohka, vol. 8 (1980), No. 2, pages 271 to 286.

(6) Balo, J. and Banga, I.: The Elastolytic Activity of Pancreatic Extracts. Biochem. J., 46, 384 (1950).

As mentioned above, the chief effect of arthrosis deformans is the degeneration of articular cartilage. The articular cartilage naturally undergoes degeneration with aging from injury or normal use, and such degeneration is accelerated by secondary factors such as wounds and interruptions in blood circulation. The degeneration of cartilage is thought to result fundamentally from a metabolic disturbance. The cartilage tissue consists of chondrocytes and extracellular substances. The latter are called the matrix substances of cartilage and consist of mucoproteins, mucopolysaccharides and collagen fibers. In the early stages of degeneration due to arthrosis deformans, levels of normal metabolic substrates decrease, and mucopolysaccharides and proteinaceous substances separate from the cartilage in the form of granules. At the same time, the collagen fiber separates into a plurality of fibers and the cartilage is converted into a frayed fiber, resembling asbestos. It is also thought that hyaluronidase penetrates the surface of the injured cartilage, destroys the matrix substances and destroys the structure of the collagen fibers. In any case, it is widely believed that the causes of arthrosis deformans are associated with the disturbance of the metabolism of mucopolysaccharides and collagen.

Accordingly, if elastase can inhibit the disruption of mucopolysaccharides or the proliferation of collagen within the articular cartilage which occur in arthrosis deformans, the repair of this arthrosis and the amelioration of the clinical symptoms thereof can be achieved.

However, it was not previously known whether or not elastase had such effects. This invention has therefore achieved an important discovery in the field of treatment of arthrosis deformans and makes it possible to substantially completely clear up arthralgia in some cases, a result which has heretofore been thought difficult to achieve.

The invention will now be described in detail.

Arthrosis deformans is a chronic painful disease in which retrogressive degeneration of articular cartilage results from congenital or acquired articular deformation and destruction of the articular load-bearing regions of the cartilage and proliferous change in the load-free regions of the cartilage. This disease is typified by gonarthrosis deformans and coxarthrosis deformans, that is, arthritic inflammation of the knee joint and hip joint, respectively. Gonarthrosis deformans and coxarthrosis deformans are particularly common forms of arthrosis deformans. This invention exhibits particularly outstanding analgesic and therapeutic effects against gonarthrosis deformans.

In this invention, elastase is preferably orally administered, absorbed by the intestinal wall and carried into the blood. In the blood, elastase combines with $\alpha_2$-macroglobulin and $\alpha_1$-antitrypsin, is distributed widely over all of the body tissues, is metabolized chiefly in the liver, and then is excreted into the urine. The concentration of elastase in the blood reaches a maximum 6 hours after administration. The area under the blood concentration curve, which represents the total amount of elastase absorbed by the blood, increases in proportion to the dosage.

The preferred daily dosage of elastase according to this invention is, for example, 2,000 to 20,000 EL. U (elastase units) per patient suffering from arthrosis deformans. Elastase is continuously administered over a period of time of, for example, from 4 to 20 weeks, at such dosages. However, this invention is not limited to the above-mentioned dosage range, since the dosage may vary according to the needs of individuals patients. The acute toxicity of elastase is shown in the following table. Acute toxicity is measured in elastase units per kilogram body weight of the test animal.

| Animal | Sex | Acute Toxicity $LD_{50}$ (EL. U/kg) | | | |
|---|---|---|---|---|---|
| | | Oral | Subctaneous | Intra-peritoneal | Intra-veneous |
| rat | male | >150,000 | >75,000 | 6,380 | 6,380 |
| | female | >150,000 | >75,000 | 5,850 | 6,380 |
| mouse | male | >150,000 | >75,000 | 4,970 | 5,100 |
| | female | >150,000 | >75,000 | 2,780 | 4,310 |

Other toxicity values are shown by the following experiments.

Subacute toxicity

Elastase was orally administered to Wistar strain female and male rats at dosages of 750, 7,500 and 37,500 or 75,000 EL. U/kg/day for 4 weeks, and to female and male beagle dogs at dosages of 900 or 4,500 EL. U/kg/day for 12 weeks. As a result, no noteworthy anomalous findings as to general physical condition, blood and urinary tests and morphological observations made visually and histologically were obtained for any of the rats and dogs.

Chronic toxicity

Elastase was orally administered to Wistar strain female and male rats at dosages of 2,250, 5,700, 11,250 or 22,500 EL. U/kg/day for 24 weeks. As a result, no anomalous findings as to general physical condition, blood and urinary tests, and visual and histological morphological observations were obtained for the rats tested.

Teratogenicity

Elastase was forcibly orally administered to pregnant mice and rats in the stage of organogenesis at dosages of 750, 7,500 or 75,000 EL. U/kg/day for 6 consecutive days. As a result, death, hindrance to growth and teratogenesis of the embryos were not observed, and there was no effect upon the morphological and functional differentiation of the newborn animals.

The pharmaceutical composition of this invention is generally orally administered. It is preferred to prepare the pharmaceutical composition of the invention as oral administrable, solid preparations, such as granules, tablets and capsules. The production of solid preparations can be carried out according to conventional methods using excipients commonly used in the art of pharmaceutical preparations. Accordingly, elastase granules are prepared by directly adding a binder to, for example, a mixture comprising elastase, lactose, starch and cellulose, or by adding a binder while spraying the foregoing mixture onto the binder as the binder moves along a fluidized bed. The thus-produced granules can be encapsulated to form capsules.

The effects of this invention are demonstrated by the clinical examples described below.

CLINICAL EXAMPLES

1. Subjects and procedures

The subjects included 18 patients (men 6 cases, women 12 cases, ages 57 to 88, average 70.9±8.2 years old) that were diagnosed negative as to rheumatoid arthrosis and were clinically diagnosed as suffering from gonarthrosis deformans. These patients had underlying diseases as shown in Table 1. Thirteen patients displayed bilateral gonarthralgia and the other five patients displayed unilateral gonarthralgia. The distribution of the duration of gonarthralgia in the patients from the onset thereof was such that six cases fell into each of the periods of (1) three years or shorter, (2) four to five years, and (3) five years or longer.

The effectiveness of elastase against gonarthrosis deformans was evaluated by administering capsules containing 1,800 EL.U elastase at a daily dosage of 3 capsules per day to each patient for 8 weeks, and investigating the severity of gonarthralgia before administration, 4 weeks after administration, and 8 weeks after administration. Curative effects were judged as "markedly effective" when the effects of gonarthralgia on motion were completely cleared up, as "effective" when the effects of gonarthralgia were palliated, as "ineffective" when there was no effect, and as "aggravated" when the effects of the gonarthralgia were made worse.

In order to eliminate psychological effects upon the measurements of effectiveness during the tests, the patients received the explanation that this drug was being administered as an antilipemic agent because it controls anomalies of blood lipid associated with arteriosclerosis, hypertension and other conditions, but the patients did not receive any explanation concerning its effectiveness against gonarthralgia. However, these patients had received and continued to receive during the test period antihypertensive agents, agents for improving cerebral circulation and other drugs for the treatment of their underlying diseases. However, the levels of these drugs in the patients' bodies remained unchanged from the day 8 weeks before the start of the test up to the last day of the test. During the tests, no patient received any other antiinflammatory, analgesic or steroid having the possible effect of palliation of arthralgia.

2. Results (1) Effectiveness against gonarthralgia

The results of the evaluations of the administration of elastase for the treatment of gonarthralgia in human patients are shown in Tables 2 and 3. As to the entire group of patients tested, there were no results of "aggravated" and only two results of "ineffective". The sixteen remaining patients showed distinct palliation or complete clearing of the gonarthralgia. Thus, the overall rate of improvement was 88.9%.

With respect to the period of administration, after 4 weeks of administration of the elastase, 6 results (33.3%) were "markedly effective", 10 results (55.6%) were "effective" and 2 results (11.1%) were "ineffective". Eight results each of "markedly effective" and "effective" (44.48%) and no change in the two results of "ineffective" were observed after 8 weeks of administration of elastase to the same patients that were previously evaluated after 4 weeks.

With respect to the effect of the duration of gonarthralgia from the onset thereof in the patient, there was one "ineffective" result in the 4 to 5 year group and one such result in the 5 years or longer group. However, there was no distinct difference in the rate of improvement between the different groups, and in two cases wherein gonarthralgia which has been present for a long time (greater than 5 years), the gonarthralgia was completely cleared up.

The patients who showed improvement perceived palliation or clearing of arthralgia at the beginning of the second week after the start of administration of elastase. When a comparison of effectiveness was made between the results after 4 weeks and the results after 8 weeks, results of "markedly effective" were somewhat higher after the 8 week period. However, no distinct difference in the rate of improvement was recognized. This indicates that the analgesic effect develops at a relatively early stage after the start of administration of elastase.

TABLE 1
Details of Subject Diseases

| No. | Case | Age | Sex | Underlying disease | Arthralgia | Duration of arthralgia from onset | Note |
| --- | --- | --- | --- | --- | --- | --- | --- |
| 1 | K. T. | 71 | man | cerebral infarction, diabetes | left knee | 3 years | paresis on the right side |
| 2 | Y. W. | 77 | woman | Parkinson's disease | knee, bilateral | >5 | |
| 3 | S. O. | 57 | woman | hypertension | knee, bilateral | 5 | |
| 4 | T. I. | 65 | woman | tension headache | knee, bilateral | 4 | stiffness in both hands for 2 years |
| 5 | Y. M. | 73 | man | polygenetic cerebral infectionn | left knee, lumbago | 3 | no motoric paralysis, mild dementia |
| 6 | Y. S. | 67 | woman | hypertension | knee, bilateral, left shoulder | 3 | so-called periarthritis numero-scapularis in the left shoulder |
| 7 | M. H. | 82 | man | cerebral infarction, asthma | knee, bilateral, lumbago | >5 | |
| 8 | K. U. | 68 | woman | hypertension | knee, bilateral | >5 | |
| 9 | M. S. | 69 | woman | hypertension | knee, bilateral | 4 | |
| 10 | M. T. | 58 | woman | hypertension | knee, bilateral | >5 | carpal tunnel syndrome |
| 11 | K. K. | 80 | woman | hypertension, TIA | knee, bilateral, lumbago | >5 | |
| 12 | K. U. | 88 | man | cerebral infarction | knee, bilateral | 5 | no motoric paralysis |
| 13 | T. U. | 81 | woman | hypertension | knee, bilateral | >5 | |
| 14 | K. H. | 75 | woman | hypertension | knee, bilateral | 2 | |
| 15 | F. Y. | 67 | woman | hypertension | knee, bilateral | 4 | carpal tunnel syndrome |
| 16 | M. G. | 72 | woman | hypertension | left knee | 5 | |
| 17 | Y. K. | 64 | man | hypertension | left knee | 3 | |
| 18 | T. M. | 62 | man | hypertension, cerebral infarction | right knee | 3 | hyperreflexia in the right tendon |

TABLE 2
Effect of Elastase Administration on Gonarthralgia

| No. | Case | Duration of gonarthralgia from onset | Effect on arthralgia after 4 w. | Effect on arthralgia after 8 w. | Side effect | Miscellaneous |
| --- | --- | --- | --- | --- | --- | --- |
| 1 | K. T. | 3 years | + | + | | |
| 2 | Y. W. | >5 | + | + | | |
| 3 | S. O. | 5 | + | ++ | transient epigastric discomfort | |
| 4 | T. I. | 4 | ++ | ++ | | morning stiffness in hands cleared, lumbago also cleared |
| 5 | Y. M. | 3 | ++ | ++ | | |
| 6 | Y. S. | 3 | + | + | transient epigastric discomfort | cinesalgia in the left shoulder not changed |
| 7 | M. H. | >5 | + | + | | lumbago lasting |
| 8 | K. U. | >5 | ++ | ++ | | |
| 9 | M. S. | 4 | + | + | transient epigastric discomfort | administration discontinued after 2 w, and restarted because of worsened arthralgia |
| 10 | M. T. | >5 | + | + | | carpal tunnel syndrome not changed |
| 11 | K. K. | >5 | + | ++ | | lumbago lasting |
| 12 | K. U. | 5 | − | − | | |
| 13 | T. U. | >5 | − | − | | |
| 14 | K. H. | 2 | ++ | ++ | | |
| 15 | F. Y. | 4 | + | + | | carpal tunnel syndrome not changed, troubles in dancing eliminated |

TABLE 2-continued

Effect of Elastase Administration on Gonarthralgia

| No. | Case | Duration of gonarthralgia from onset | Effect on arthralgia after 4 w. | after 8 w. | Side effect | Miscellaneous |
|---|---|---|---|---|---|---|
| 16 | M. G. | 5 | ++ | ++ | | |
| 17 | Y. K. | 3 | ++ | ++ | | |
| 18 | T. M. | 3 | + | + | | |

++ markedly effective
+ effective
− ineffective

TABLE 3

Rate of Effectiveness Analyzed from Duration of Gonarthralgia

| Effectiveness | Duration of arthralgia | | | | | | | |
|---|---|---|---|---|---|---|---|---|
| | 3 years or shorter | | 4 to 5 years | | 5 years or longer | | Overall | |
| | Term of administration | | | | | | | |
| | 4 w | 8 w | 4 w | 8 w | 4 w | 8 w | 4 w | 8 w |
| markedly effective | 3 | 3 | 2 | 3 | 1 | 2 | 6 | 8 |
| effective | 3 | 3 | 3 | 2 | 4 | 3 | 10 | 8 |
| ineffective | 0 | 0 | 1 | 1 | 1 | 1 | 2 | 2 |
| aggravated | 0 | 0 | 0 | 0 | 0 | 0 | 0 | 0 |
| rate of effectiveness | 6/6 100% | 6/6 100% | 5/6 83.3% | 5/6 83.3% | 5/6 83.3% | 5/6 83.3% | 16/18 88.9% | 16/18 88.9% |

Several typical case histories of patients for whom "markedly effective" and "ineffective" results were obtained are given below.

T.I. (Case 4, result—markedly effective, 65-year old woman) was a patient who had a vague pain in the occipital region and a stiff shoulder for 5 years and consulted a physician, but had no distinct neurological local symptoms and was under observation for tension headaches. About 4 years ago, she began to complain of bilateral gonarthralgia which caused pain when she stood up from a sitting position or when she went up or down steps. Crepitation was present in the knee joints on both sides. Further, she had morning stiffness in the fingers of her hands for about 2 years.

Administration of elastase at the above-mentioned dosage was started. After 4 weeks, the cinesalgia in the knee joints was completely cleared up, and morning stiffness in the fingers also was cleared up.

U.K. (Case 8, result—markedly effective, 68-year old woman) was a patient who had hypertension (blood pressure about 160 to 180/90 mm Hg) for about 10 years and consulted a physician for the purpose of controlling her blood pressure. About 4 years ago, she began to complain of arthralgia in the knee on both sides which occurred when she stood up from a sitting position, when she started walking or when she would go up or down steps. She received drainage of joint fluid and intra-articular steroid injections as treatments for gonarthrosis deformans several times over the last 5 years. She had mild dilatation of the heart. Her knee joints both sides did not show redness but showed swelling and crepitation.

Administration of elastase was begun as described above. After 4 weeks, the patient said that the pain in her knees had disappeared entirely, and she stopped complaining of having difficulty in standing up and of going up and down steps. As a drug used in combination with the elastase, trichlormethiazide at a dosage of 4 mg/day was used to treat her hypertension.

M.G. (Case 16, result—markedly effective, 72-year old woman) consulted a physican for hypertension and a stiff shoulder as her main problems. She engaged in Japanese dancing, and she had a pain in the left knee for about 5 years which has made it difficult for her to stand up from the sitting position in the formal manner, and when doing so she felt a strong pain in the left knee joint. No particular anomalies were present in the chest and the abdomen. Crepitation was present upon flexion of the left knee. Swelling of the joints was not very distinct.

Administration of elastase was begun as described above. After 4 weeks, the pain in the left knee was completely cleared up, and this patient said that her problems with Japanese dancing had disappeared.

T.U. (Case 13, result—ineffective, 81-year old woman) had hypertension for about 15 years and consulted a physician for the purpose of a precise examination. She had cinesalgia in the knees on both sides for about 15 years, and she receive intra-articular steroid injections many times. When standing up or going up and down steps, she felt a distinct pain in her knee joints. Her gait was aided by a cane or a helper. Her knee joints showed swelling and distinct crepitation. An X-ray image of the knee joints showed that the joint gaps on both sides were narrowed, irregularities were present on the surface of the joint, and sclerosis of subcartilagious bone was present. In the periarticular region, distinct formation of osteophytes was observed and the joint on the whole had a destroyed appearance.

Administration of elastase was begun as described above, but no improvement was recognized after either 4 weeks or 8 weeks of treatment with elastase.

(2) Effectiveness against other types of arthralgia

In the foregoing clinical examples, there were 3 cases in which the patients had gonarthralgia combined with lumbago probably resulting from lumbar vertebrae deformans. In one of these cases, Case 5, the lumbago also cleared up during the term of administration of the elastase. In Case 6, the patient had cinesalgia in the left shoulder, that is, periarthritis humeroscapularies. No change in this condition was observed during the term of administration of elastase. In Cases 10 and 15, the patients frequently complained of anomalies of sensation, particularly in the second through the fourth fingers, but this symptom was not cleared up by the administration of elastase. In all of these cases, however, gonarthralgia was palliated or cleared up by the action of elastase.

(3) Side effects

Transient epigastric discomfort was observed as an anomalous side effect for some subjects during the term of administration of the elastase. In Cases 3, 6 and 9, the patients suffered from epigastric discomfort for several days one to two weeks after the administration of elastase began. In Cases 3 and 6, the epigastric discomfort then disappeared after 4 weeks. In Case 9, the administration of elastase was discontinued at the beginning of the second week because of epigastric discomfort. However, because the pain in the patient's knee joints worsened when the administration of elastase was discontinued, the patient realized the palliative effect of the drug on gonarthralgia, and the administration of elastase was therefore restarted at the beginning of the third week, with consequent palliation of gonarthralgia. The administration of elastase was thus continued in this case and the epigastric discomfort cleared up after 4 weeks. In none of the cases were nausea, vomiting, exanthema or the like observed.

Conclusions

The following results were obtained by the foregoing clinical examples wherein elastase was administered for 8 weeks to 18 patients suffering from gonarthrosis deformans and attendant gonarthralgia:

(1) Four weeks after administration, in 6 out of the 18 cases, the elastase administrations showed such a marked effectiveness that the arthralgia was completely cleared up, and in 10 of the 18 cases, arthralgia was considerably palliated so that these cases were judged as results of "effective". Two cases were judged as results of "ineffective". No cases were found wherein "aggravated" was the result.

(2) Eight weeks after the administration of elastase began, 8 out of the 18 cases obtained "markedly effective" results, 8 cases were judged as "effective" results, 2 cases were judged as "ineffective" and no cases were judged as "aggravated". The overall rate of improvement was 88.9%, which is very high. The rate of "markedly effective" was 44.4%, the rate of "effective" was 44.4%, the rate of "ineffective" was 11.1%, and the rate of "aggravated" was 0%.

(3) In 3 cases (16.7%), epigastric discomfort was observed as a side effect, but the administration of elastase was not discontinued in any of these cases.

The above results strongly suggest that elastase is extremely effective against arthralgia in gonarthrosis deformans. It is particularly noteworthy that an excellent analgesic action can be obtained at an early stage of the term of administration of elastase.

It is believed that elastase has a decomposing action not only upon elastin but also upon mucopolysaccharides. Therefore, it can be assumed that elastase has an effect upon anomalies of mucopolysaccharides or collagen which underlie arthrosis deformans. However, with respect to the analgesic effect of elastase shown in the clinical examples, it is difficult to interpret this as anything other than repair of the matrix structure of the cartilage. This is suggested because the analgesic effect is obtained at an extremely early stage of treatment, but it is difficult to understand, in cases of advanced arthrosis deformans where the condition has been present for a long time, how the knee cartilage can be repaired by short-term administration of elastase.

In any event, the effectiveness of the pharmaceutical composition of this invention against arthrosis deformans is powerfully indicated by the fact that, when the composition containing elastase of this invention was administered to patients without informing them of the relation between this composition and gonarthralgia, persistent gonarthralgia was considerably palliated or completely cleared up during the term of administration for most of the patients.

The present invention will now be described in further detail with reference to the following examples of pharmaceutical compositions according to the invention.

EXAMPLE 1

100 g of elastase (85 EL. U/mg) together with 400 g of sucrose fatty acid ester were mildly triturated to form a uniform powder. To this powder were added 500 g of spray-dried lactose, 495 g of crystalline cellulose and 300 g of CMC calcium, and the mixture was agitated. Then, 5 g of calcium stearate was added to the mixture through an 80-mesh sieve and uniformly mixed therein, and the resulting mixture was formed into tablets each weighing 180 mg. These tablets were used as a therapeutic drug for the treatment of arthrosis deformans.

EXAMPLE 2

The following amounts of the ingredients described below were used in this example:

| Nomparel | 2.5 kg |
| HPC-L | 0.5 kg |
| elastase (85 EL. U/mg) | 0.6 kg |
| sucrose fatty acid ester | 1.5 kg |
| cornstarch | 2.7 kg |
| HP-55 | 1.95 kg |
| acetyl monoglyceride | 0.25 kg |
| ethanol | q.s. |

A centrifugal fluid coater was charged with the Nomparel. While an ethanolic solution of HPC-L was being sprayed therein, a mixed powder of elastase, sucrose fatty acid ester and cornstarch was also dispersed therein, and the resulting mixture was granulated. The produced granules were spray-coated with an ethanoloc solution of acetyl monoglyceride and HP-55 by means of the above apparatus to produce enteric granules. These granules were used as a therapeutic drug for treatment of arthrosis deformans. Nomparel is a mixture of sucrose and cornstarch, HPC-L is hydroxypropylcellulose and HP-55 is hydroxypropylmethylcellulose phthalate.

The embodiments of the invention in which an exclusive property or privilege is claimed are defined as follows:

1. A method for treating a subject suffering from arthrosis deformans which comprises administering to said subject a therapeutically effective amount of a composition comprising elastase and a pharmacologically acceptable carrier.

2. A method as claimed in claim 1, wherein said subject is a human being.

3. A method as claimed in claim 2, wherein said subject is suffering from gonarthrosis deformans.

4. A method as claimed in claim 2, wherein said subject is suffering from coxarthrosis deformans.

5. A method as claimed in claim 1, wherein said elastase is porcine elastase.

6. A method as claimed in claim 5, wherein said porcine elastase has a molecular weight of 25,900, an isoelectric point of pH $9.5 \pm 0.5$, and a sedimentation coefficient $S_{20,w}$ of 2.6.

7. A method as claimed in claim 2, wherein said composition is administered orally.

8. A method according to claim 7, wherein said composition is administered to said human subject at a dosage in the range of from 2,000 to 20,000 EL. U day.

9. A method according to claim 8, wherein said composition is administered to said human subject over a period in the range of from 4 to 20 weeks.

10. A method according to claim 9, wherein said composition consists essentially of elastase, lactose, starch, cellulose and a binder, and is formulated into a solid preparation selected from the group consisting of granules, tablets and capsules.

* * * * *